United States Patent [19]

DeCaul et al.

[11] Patent Number: 5,004,856
[45] Date of Patent: Apr. 2, 1991

[54] PROCESS FOR UPGRADING METHANE TO HIGHER HYDROCARBONS

[75] Inventors: Lorenzo C. DeCaul, Chester, Pa.; Scott Han, Lawrenceville; Robert E. Palermo, Bloomfield, both of N.J.; Dennis E. Walsh, Richboro, Pa.

[73] Assignee: Mobil Oil Corporation, Fairfax, Va.

[21] Appl. No.: 459,218

[22] Filed: Dec. 29, 1989

[51] Int. Cl.$^5$ ............................................. C07C 2/00
[52] U.S. Cl. .................... 585/500; 585/943; 585/654; 585/658; 585/661; 585/662; 585/700; 585/415; 585/417; 585/418; 585/541; 585/663
[58] Field of Search .............. 585/943, 500, 654, 658, 585/661, 662, 663, 700, 415, 417, 418, 541

[56] References Cited

U.S. PATENT DOCUMENTS

| | | | |
|---|---|---|---|
| 4,443,649 | 4/1984 | Jones et al. | 585/500 |
| 4,523,049 | 6/1985 | Jones et al. | 585/500 |
| 4,608,449 | 8/1986 | Baerns et al. | 585/500 |
| 4,665,259 | 5/1987 | Brazdil et al. | 585/500 |

*Primary Examiner*—Chung K. Pak
*Attorney, Agent, or Firm*—Alexander J. McKillop; Charles J. Speciale; Edward F. Kenehan, Jr.

[57] ABSTRACT

There is provided a process for the direct partial oxidation of methane with oxygen, whereby hydrocarbons having at least two carbon atoms are produced. The catalyst used in this reaction is a cadmium-manganese oxide catalyst.

8 Claims, No Drawings

PROCESS FOR UPGRADING METHANE TO HIGHER HYDROCARBONS

BACKGROUND

There is provided a process for the direct partial oxidation of methane with oxygen, whereby hydrocarbons having at least two carbon atoms are produced. The catalyst used in this reaction is a cadmium-manganese oxide catalyst.

Natural gas is an abundant fossil fuel resource. Recent estimates places worldwide natural gas reserves at about $35 \times 10^4$ standard cubic feet, corresponding to the energy equivalent of about 637 million barrels of oil.

The composition of natural gas at the wellhead varies but the major hydrocarbon present is methane. For example the methane content of natural gas may vary within the range of from about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Processed natural gas, consisting essentially of methane, (typically 85-95 volume percent) may be directly used as clean burning gaseous fuel for industrial heat and power plants, for production of electricity, and to fire kilns in the cement and steel industries. It is also useful as a chemicals feedstock, but large-scale use for this purpose is largely limited to conversion to synthesis gas which in turn is used for the manufacture of methanol and ammonia. It is notable that for the foregoing uses no significant refining is required except for those instances in which the wellhead-produced gas is sour, i.e., it contains excessive amounts of hydrogen sulfide. Natural gas, however, has essentially no value as a portable fuel at the present time. In liquid form, it has a density of 0.415 and a boiling point of minus 162° C. Thus, it is not readily adaptable to transport as a liquid except for marine transport in very large tanks with a low surface to volume ratio, in which unique instance the cargo itself acts as refrigerant, and the volatilized methane serves as fuel to power the transport vessel. Large-scale use of natural gas often requires a sophisticated and extensive pipeline system.

A significant portion of the known natural gas reserves is associated with fields found in remote, difficulty accessible regions. For many of these remote fields, pipelining to bring the gas to potential users is not economically feasible.

Indirectly converting methane to methanol by steam-reforming to produce synthesis gas as a first step, followed by catalytic synthesis of methanol is a well-known process. Aside from the technical complexity and the high cost of this two-step, indirect synthesis, the methanol product has a very limited market and does not appear to offer a practical way to utilize natural gas from remote fields. The Mobil Oil Process, developed in the last decade provides an effective means for catalytically converting methanol to gasoline, e.g. as described in U.S. Pat. No. 3,894,107 to Butter et al. Although the market for gasoline is huge compared with the market for methanol, and although this process is currently used in New Zealand, it is complex and its viability appears to be limited to situations in which the cost for supplying an alternate source of gasoline is exceptionally high. There evidently remains a need for other ways to convert natural gas to higher valued and/or more readily transportable products.

One approach to utilizing the methane in natural gas is to convert it to higher hydrocarbons (e.g. $C_2H_6$; $C_2H_4$; $C_3H_8$; $C_3H_6$...); these have greater value for use in the manufacture of chemicals or liquid fuels. For example, conversion of methane to ethane or ethylene, followed by reaction over a zeolite catalyst can provide a route to gasoline production that entails fewer steps than the indirect route via methanol synthesis described above. Unfortunately, the thermal conversion of methane to ethane is a thermodynamically unfavorable process ($\Delta G° > +8$ kcal/mol $CH_4$) throughout the range from 300–1500K. The upgrading reactions explored here are oxidative conversions of methane to higher hydrocarbons, as exemplified in the following equations.

$$CH_4 + 0.25O_2 \rightarrow 0.5C_2H_6 + 0.5H_2O$$

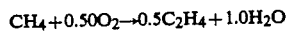

$$CH_4 + 0.5O_2 \rightarrow 0.5C_2H_4 + 1.0H_2O$$

Analogous reactions include those converting methane to $C_3$, $C_4$, ... and higher hydrocarbons. These oxidation processes have very favorable free energy changes ($\Delta G° < -19$ kcal/mol $CH_4$) throughout the temperature range of 300–1000K. The oxidation reactions are commonly performed in the presence of a catalyst. The use of the catalyst allows the reaction to occur under conditions where there is essentially no thermal reaction between methane and oxygen. The catalyst can also favorably influence the selectivity of the oxidation reaction to minimize the extent of over-oxidation to CO and $CO_2$.

SUMMARY

There is provided a process for synthesizing one or more hydrocarbons having at least two carbon atoms by the direct partial oxidation of methane, said process comprising contacting a mixture of methane and oxygen with a cadmium-manganese oxide catalyst under sufficient conversion conditions. After this conversion, the one or more hydrocarbons may be recovered.

The cadmium-manganese oxide composition provides superior selectivity to $C_2+$ products (i.e. products having 2 or more carbon atoms) vs. that obtained with simple manganese oxides or that of manganese in combination with other divalent ions such as magnesium.

EMBODIMENTS

The cadmium-manganese oxide catalyst comprises a mixture of cadmium and manganese in oxide form. One method of preparing this catalyst is by calcining a suitable physical mixture of cadmium and manganese compounds, for example a mixture of $Cd(OH)_2$ and $Mn_2O_3$. Alternatively, the catalyst may be prepared by impregnating a solution of one compound onto the solid form of another compound, for example impregnating a solution of $Cd(NO)_2$ onto a manganese oxide, followed by a suitable calcination. Similarly, solutions of both cadmium and manganese compounds can be coevaporated and/or precipitated, and the resulting materials calcined. Metal compounds that might be employed in these preparations include the oxides, hydroxides, acetates, carbonates, sulfates, nitrates, nitrites, or halides of manganese or cadmium, as well as metal complexes of manganese and/or cadmium. Catalytic performance of the resulting material may be a function of the composition (in terms of wt-% Cd or Mn) as well as the manner of catalyst preparation. The catalyst may contain, for example, at least 10 weight percent of Cd and at least 10 weight percent of Mn, based upon the total weight of Cd and Mn in the cadmium-manganese oxide.

In the practice of the present invention, it is preferred to use a dual flow system, i.e., a system in which the methane and the oxygen or air are kept separate until mixed just prior to being introduced into the reactor. However, if desired, the oxygen and methane may be premixed and stored together prior to the reaction. The preferred dual flow system minimizes the risk of fire or explosion. The methane feed for the present reaction may be provided by pure methane or by a methane containing gas, e.g., containing at least 50 percent by weight methane. An example of a methane feed is natural gas.

Air may be used instead of oxygen; inert diluents such as nitrogen, argon, helium, steam or $CO_2$ may also be cofed. The gas comprising the methane may be derived from processed natural gas. In the system, the amount of oxygen is controlled so as to prepare a reaction mixture where the volume ratio of methane to oxygen is within the range of 0.1-100:1, more preferably in the range of 1-50:1, even more preferably in the range of 1-10:1. The operating pressure for the reactants (methane and oxygen) may be within the range of 0.1 to 30 atmospheres, preferably within the range of 0.5-5 atm. The flow rate of the feed gas over the catalyst may be expressed as the volumetric gas flow rate at ambient temperature and pressure divided by the volume of catalyst, giving the Gas Hourly Space Velocity (GHSV) in units of $h^{-1}$. Preferred GHSV is within the range of 10-100,000 $h^{-1}$, more preferably within the range of 50-50,000 $h^{-1}$. The GHSV may be chosen to maximize the selectivity to higher hydrocarbon products, to maximize the yield of higher hydrocarbon products, or to maximize the conversion of either methane or oxygen reactant.

The temperature in the reaction zone may be from about 300° C. to 1200° C., and preferably from about 500° C. to 1000° C., more preferably from 600° C. to 900° C.

EXAMPLE

The following terms are defined. Methane conversion: the percentage of carbon atoms in the feed converted to other products. $C_{2}+$ selectivity: percentage of carbon atoms derived from converted methane which ends up as $C_2H_6$, $C_2C_4$, $C_3H_8$, $C_3H_6$, . . . (i.e. higher hydrocarbons, non-$CO_x$). $C_{2}+$ yield: the percentage of total feed carbon which ends up as higher hydrocarbons (i.e. conversion X selectivity).

Catalyst A was prepared by high temperature reaction (900° C.) of a mixture of $Cd(OH)_2$ and $Mn_2O_3$; composition of the final material was checked by elemental analysis. Catalyst B was prepared by impregnating $Mn_2O_3$ with an aqueous solution of $Cd(NO_3)_2$. The impregnated solid was dried at 150° C., followed by intervals of calcination at 350° C. and 900° C. A magnesium-manganese oxide catalyst was prepared by high temperature reaction of the solids MgO and $Mn_3O_4$. Unmodified oxides, $Mn_2O_3$ and $Mn_3O_4$, and were obtained from commercial sources and were used as supplied. Reactions were run in a 14 mm ID×140 mm length quartz reactor; 0.1 g of 230/325 mesh catalyst was mixed with 4 g of 50 mesh quartz chips and loaded into the reactor along with additional pre- and post-beds of quartz sufficient to fill the reactor volume. Feed gases were delivered at atmospheric pressure from mass flow controllers. The temperature in the catalyst bed was measured through a quartz thermowell and ranged from 750°-760° C. The catalysts were conditioned in the reactor at 750° C. for 1 h under $O_2$ (25 cc/min) prior to starting the feed of 25 mol% $CH_4$, 5 mol% $O_2$, 70 mol% $N_2$ (space velocities given in the table are for gas flow rates measured at ambient conditions). Water produced in the reaction was condensed from the effluent into a chilled trap (−3° C.) and the product gas was analyzed on a Carle refinery gas analyzer. In the absence of a catalyst, there is no reaction of methane under the specified conditions.

Table I gives the $CH_4$ conversion and $C_{2}+$ selectivity for the examined catalyst; note the given data allows for comparison of the selectivity at essentially constant methane conversion. The cited data for all these examples were taken after the systems had reached stable operation (2-18 h). The $C_{2}+$ selectivity of the cadmium-promoted materials ($\geq 32.5\%$) is superior to the unmodified manganese oxides ($\leq 19.3\%$), and likewise is superior to the magnesium modified manganese oxide (0.0%).

TABLE I

Comparison of Oxidative Coupling Results for Cadmium-Promoted Manganese Oxides.

| Catalyst | Space Velocity (cc/m/g cat) | $CH_4$ Conv. (% C) | $C_2+$ Sel. (% C) |
|---|---|---|---|
| Catalyst A Cd/Mn/$O_x$ (35.2 wt % Cd, 39.0 wt % Mn) | 500 | 11.6 | 62.5 |
| Catalyst B Cd/Mn/$O_x$ (21.3 wt % Cd, 53.2 wt % Mn) | 1000 | 10.4 | 32.5 |
| $Mn_2O_3$ | 1000 | 9.8 | 19.3 |
| $Mn_3O_4$ | 1000 | 9.7 | 0.0 |
| Mg/Mn/$O_x$ (12.6 wt % Mg, 54.4 wt % Mn) | 500 | 8.0 | 0.0 |

What is claimed is:

1. A process for synthesizing one or more hydrocarbons having at least two carbon atoms by the direct partial oxidation of methane, said process comprising contacting a mixture of methane and oxygen with a cadmium-manganese oxide catalyst under conditions sufficient to convert methane to said one or more hydrocarbons having at least two carbon atoms.

2. A process according to claim 1, wherein said cadmium-manganese oxide catalyst is prepared by calcining a mixture of $Cd(OH)_2$ and $Mn_2O_3$.

3. A process according to claim 1, wherein said conversion conditions include a temperature of from about 300° C. to about 1200° C. and a reactant partial pressure of from about 0.1 atm to about 30 atm.

4. A process according to claim 1, wherein said mixture of methane and oxygen has a volume ratio of methane to oxygen of 0.1-100:1.

5. A process according to claim 1, wherein said mixture of methane and oxygen is provided by a mixture of natural gas and air.

6. A process according to claim 3, wherein said conversion conditions include a Gas Hourly Space Velocity of from 10 to 100,000 $h^{-1}$.

7. A process according to claim 4, wherein said conversion conditions include a temperature of from 600° C. to 900° C., a reactant partial pressure of from 0.5 to 5 atm and a Gas Hourly Space Velocity of from 50 to 50,000 $n^{-1}$.

8. A process according to claim 7, wherein said mixture of methane and oxygen has a volume ratio of methane to oxygen of 1-10:1.

* * * * *